(12) United States Patent
Liao

(10) Patent No.: US 8,268,171 B2
(45) Date of Patent: Sep. 18, 2012

(54) BOTTOM CONTROL TYPE SPECIMEN FILTERING CONTAINER AND FILTERING METHOD THEREOF

(76) Inventor: Qinghua Liao, Xiamen (CN)

( * ) Notice: Subject to any disclaimer, the term of this patent is extended or adjusted under 35 U.S.C. 154(b) by 0 days.

(21) Appl. No.: 13/264,954

(22) PCT Filed: Apr. 28, 2010

(86) PCT No.: PCT/CN2010/072273
§ 371 (c)(1),
(2), (4) Date: Oct. 17, 2010

(87) PCT Pub. No.: WO2010/124633
PCT Pub. Date: Nov. 4, 2010

(65) Prior Publication Data
US 2012/0037563 A1 Feb. 16, 2012

(30) Foreign Application Priority Data
Apr. 28, 2009 (CN) ...................... 2009 2 0151032 U

(51) Int. Cl.
*B01D 35/02* (2006.01)
*B01L 3/00* (2006.01)
*B01L 3/14* (2006.01)
*G01N 33/48* (2006.01)
*G01N 1/28* (2006.01)

(52) U.S. Cl. ...................... 210/233; 210/235; 210/416.1; 210/251; 422/527; 422/549; 422/550

(58) Field of Classification Search .................. None
See application file for complete search history.

(56) References Cited

U.S. PATENT DOCUMENTS
3,302,462 A * 2/1967 Pursell ...................... 73/864.15
(Continued)

FOREIGN PATENT DOCUMENTS
CN         2457588        10/2001
(Continued)

*Primary Examiner* — Robert James Popovics
(74) *Attorney, Agent, or Firm* — Hamre, Schumann, Mueller & Larson, P.C.

(57) ABSTRACT

A bottom control type specimen filtering container consists of a seal plug (1), a top cap (2), a cylinder body (3), a piston rod (5), pistons (6), a clutch spring (7), a drainage needle (8) and a bottom cap (9). The piston rod (5) is disposed in a central hole (12) at the bottom of the cylinder body (3). The pistons (6) are tightly sleeved on the projections of the piston rod (5). The drainage needle (8) is fixedly connected to the lower end of the piston rod (5) through screw thread. One end of the clutch spring (7) is pressed against the bottom of the cylinder body (3), and the other end is against a flange of the drainage needle (8). Furthermore, a double-layer filtering system composed of a first layer of filter screen (4) and a second layer of filter screen (11) is arranged in the specimen filtering container. The shaft of the first layer of filter screen (4) penetrates through a middle hole of the second layer of filter screen (11) and is fixed in a hole at the top of the piston rod (5). A filtering method comprises the following steps: charging a solution to be filtered into the cylinder body (3); removing the bottom cap (9), and disposing a receiving container below the drainage needle (8); and pushing up the receiving container so as to open the bottom of the cylinder body (3) and discharge the solution from the bottom of the cylinder body (3) to the receiving container.

5 Claims, 5 Drawing Sheets

U.S. PATENT DOCUMENTS

| | | | | |
|---|---|---|---|---|
| 3,591,003 | A * | 7/1971 | Cooper | 210/90 |
| 3,705,100 | A * | 12/1972 | Blatt et al. | 604/6.04 |
| 3,939,822 | A * | 2/1976 | Markowitz | 600/575 |
| 3,969,250 | A * | 7/1976 | Farr | 210/359 |
| 3,969,925 | A * | 7/1976 | Niskin | 73/863.23 |
| 3,982,899 | A * | 9/1976 | Kelm | 73/864.18 |
| 4,063,460 | A * | 12/1977 | Svensson | 73/864.52 |
| 4,578,244 | A * | 3/1986 | Cosgrove et al. | 422/65 |
| 4,957,637 | A * | 9/1990 | Cornell | 210/782 |
| 5,077,012 | A * | 12/1991 | Guirguis | 422/401 |
| 5,089,424 | A * | 2/1992 | Khalil et al. | 436/518 |
| 5,106,583 | A * | 4/1992 | Raysberg et al. | 422/64 |
| 5,160,624 | A * | 11/1992 | Clay et al. | 210/634 |
| 5,163,582 | A * | 11/1992 | Godolphin et al. | 222/1 |
| 5,173,188 | A * | 12/1992 | Winter et al. | 210/634 |
| 5,198,197 | A * | 3/1993 | Clay et al. | 422/256 |
| 5,253,981 | A * | 10/1993 | Yang et al. | 417/3 |
| 5,268,102 | A * | 12/1993 | Clay et al. | 210/634 |
| 5,268,103 | A * | 12/1993 | Jameson et al. | 210/634 |
| 5,296,145 | A * | 3/1994 | Allington et al. | 210/541 |
| 5,322,515 | A * | 6/1994 | Karas et al. | 604/192 |
| 5,358,690 | A * | 10/1994 | Guirguis | 422/420 |
| 5,514,341 | A | 5/1996 | Urata et al. | |
| 5,533,518 | A * | 7/1996 | Vogler | 600/573 |
| 5,578,459 | A * | 11/1996 | Gordon et al. | 135/29 |
| 5,603,845 | A * | 2/1997 | Holm | 210/782 |
| 5,614,089 | A * | 3/1997 | Allington et al. | 210/198.2 |
| 5,690,828 | A * | 11/1997 | Clay et al. | 210/634 |
| 5,738,498 | A * | 4/1998 | Allington et al. | 417/53 |
| 5,741,428 | A * | 4/1998 | Holm | 210/749 |
| 5,750,027 | A * | 5/1998 | Allington et al. | 210/511 |
| 5,776,336 | A * | 7/1998 | Holm | 210/206 |
| 5,792,344 | A * | 8/1998 | Holm | 210/117 |
| 6,027,655 | A * | 2/2000 | Holm | 210/749 |
| 6,045,759 | A * | 4/2000 | Ford et al. | 422/501 |
| 6,056,921 | A * | 5/2000 | Rao et al. | 422/65 |
| 6,117,394 | A * | 9/2000 | Smith | 422/513 |
| 6,192,945 | B1 * | 2/2001 | Ford et al. | 141/2 |
| 6,294,088 | B1 * | 9/2001 | Allington et al. | 210/198.2 |
| 6,319,410 | B1 * | 11/2001 | Allington et al. | 210/634 |
| 6,416,713 | B1 * | 7/2002 | Ford et al. | 422/63 |
| 6,544,799 | B1 * | 4/2003 | Lewis et al. | 436/180 |
| 6,569,672 | B1 * | 5/2003 | Laugharn et al. | 435/286.6 |
| 6,630,652 | B2 * | 10/2003 | Jennings | 219/679 |
| 6,669,909 | B2 * | 12/2003 | Shvets et al. | 422/502 |
| 6,945,128 | B2 * | 9/2005 | Ford et al. | 73/864.16 |
| 6,979,307 | B2 * | 12/2005 | Beretta et al. | 604/6.01 |
| 7,201,875 | B2 * | 4/2007 | Norton et al. | 422/73 |
| 7,238,164 | B2 * | 7/2007 | Childers et al. | 604/6.11 |
| 7,264,780 | B1 * | 9/2007 | Sanner | 422/554 |
| 7,288,186 | B2 * | 10/2007 | Harris | 210/108 |
| 7,378,058 | B2 * | 5/2008 | Lemme et al. | 422/523 |
| 7,470,541 | B2 * | 12/2008 | Copeland et al. | 436/46 |
| 7,534,349 | B2 * | 5/2009 | Collins et al. | 210/258 |
| 7,544,326 | B2 * | 6/2009 | Norton et al. | 422/73 |
| 7,708,152 | B2 * | 5/2010 | Dorian et al. | 210/512.3 |
| 7,727,480 | B2 * | 6/2010 | Tajima | 422/547 |
| 7,744,820 | B2 * | 6/2010 | Togawa et al. | 422/535 |
| 7,951,335 | B2 * | 5/2011 | Tajima | 422/504 |
| 7,951,336 | B2 * | 5/2011 | Tajima | 422/504 |
| 7,987,995 | B2 * | 8/2011 | Dorian et al. | 210/380.1 |
| 7,988,916 | B2 * | 8/2011 | Bremauer | 422/75 |
| 8,057,760 | B2 * | 11/2011 | Tajima | 422/547 |
| 2003/0039589 | A1 * | 2/2003 | Smith | 422/100 |
| 2003/0099576 | A1 * | 5/2003 | Li et al. | 422/100 |
| 2003/0143752 | A1 * | 7/2003 | Feldsine et al. | 436/164 |
| 2003/0164333 | A1 * | 9/2003 | Nohren et al. | 210/650 |
| 2004/0052689 | A1 * | 3/2004 | Yao | 422/100 |
| 2004/0065622 | A1 * | 4/2004 | Ferguson | 210/741 |
| 2005/0135972 | A1 * | 6/2005 | Lemme et al. | 422/100 |
| 2006/0139631 | A1 * | 6/2006 | Feldsine et al. | 356/244 |
| 2006/0175242 | A1 * | 8/2006 | Dorian et al. | 210/321.68 |
| 2006/0207939 | A1 * | 9/2006 | Allington et al. | 210/656 |
| 2006/0273050 | A1 * | 12/2006 | Higgins et al. | 210/787 |
| 2009/0221080 | A1 * | 9/2009 | Tajima | 436/43 |
| 2009/0283460 | A1 * | 11/2009 | Collins et al. | 210/95 |
| 2009/0294385 | A1 * | 12/2009 | Tajima et al. | 210/808 |
| 2010/0173330 | A1 * | 7/2010 | Fulton et al. | 435/7.9 |
| 2010/0181251 | A1 * | 7/2010 | Alspektor | 210/637 |
| 2010/0206798 | A1 * | 8/2010 | Dorian et al. | 210/267 |
| 2011/0020196 | A1 * | 1/2011 | Grippi et al. | 422/535 |
| 2012/0037563 | A1 * | 2/2012 | Liao | 210/634 |

FOREIGN PATENT DOCUMENTS

| | | |
|---|---|---|
| CN | 201384885 | 1/2010 |
| CN | 201404734 | 2/2010 |
| JP | 2004-138502 | 5/2004 |
| WO | WO 2010124633 A1 * | 11/2010 |

* cited by examiner

- PRIOR ART -

BOTTOM CONTROL TYPE SPECIMEN FILTERING CONTAINER AND FILTERING METHOD THEREOF

FIELD OF INVENTION

The present invention relates to a filtering device and filtering method, and more particularly to a bottom control type specimen filtering container and filtering method thereof.

BACKGROUND OF INVENTION

In a field like medical laboratory or biology laboratory, a liquid sample such as feces, urine or river water needs to be filtered by a filtering container. The filtering container in the prior arts, for example, a disposable feces concentration container is illustrated in FIGS. 1 and 2. In FIG. 1, a safety catch 101 at the top of the container is removed manually and then a hole at the bottom of the container is pierced by a finger to allow the liquid flowing downwardly to pass through the filter screen at the bottom. Alternatively, in FIG. 2, the safety plug 202 at a side of the container is pulled manually to open the center hole and allow the liquid flowing downwardly. The prior arts have the defects that the container is just opened by the manual control of the top safety catch or the side safety plug and cannot be shut, and the filtering amount cannot be controlled so that all the liquid in the container must be filtered at a time.

SUMMARY OF THE INVENTION

The present invention is directed to provide a bottom control type specimen filtering container and filtering method, which realizes graded filtering for liquid in the container.

To achieve the above objectives, the present invention provides technical solutions.

A bottom control type specimen filtering container includes a seal plug, a top cap, a cylinder body, a piston rod, pistons, a clutch spring, a drainage needle and a bottom cap. The piston rod is disposed in a central hole at the bottom of the cylinder body. The pistons are tightly sleeved on the projections of the piston rod. The drainage needle is fixedly connected to a lower end of the piston rod through screw thread. One end of the clutch spring is pressed against the bottom of the cylinder body and the other end is pressed against a flange of the drainage needle. A double-layer filtering system composed of a first layer of filter screen and a second layer of filter screen is arranged. A shaft of the first layer of filter screen penetrates through a middle hole of the second layer of filter screen and is fixed in a hole at the top of the piston rod.

The bottom control type specimen filtering container further includes a sampler which is mounted in a designated hole of the top cap.

A clearance exists between a lower end surface of the first layer of filter screen and an upper end surface of the pistons, and a height of the clearance is greater than a thickness of the second layer of filter screen.

A bottom control type specimen filtering method includes the steps of:

step 1, for a liquid specimen, directly charging a solution to be filtered into the cylinder body and attaching the top cap; for a solid specimen, charging a solid specimen into a cylinder body, attaching the top cap and the seal plug, piercing a soft hole reserved at a center of the seal plug by a device like a syringe, charging a liquid for dissolving the solid specimen into the cylinder body and shaking evenly;

step 2, removing the bottom cap and disposing a receiving container below the drainage needle;

step 3, pushing up the receiving container to compress the clutch spring, so as to move the drainage needle upwardly together with the pistons, the piston rod and the double-layer filtering system in the cylinder body, opening the bottom of the cylinder body and discharge the solution from the bottom of the cylinder body to receiving container; and step 4, when the specimen solution is collected to a required amount, moving the receiving container downwardly, resetting the drainage needle together with the pistons, the piston rod and the double-layer filtering system by the clutch spring, shutting the bottom of the cylinder body till now the filtering is accomplished.

Based on the above technical solutions, the present invention directly controls the open or shut of the container for the specimen solution by a tube or another receiving container namely the specimen filtering container in use, and has the advantages of sanitation, good sealing property, open-and-shut ability, and capability of controlling the filtering amount, thus achieving the graded filtration of the liquid in the container depending on the requirements.

The present invention will be illustrated in details hereinafter with reference to the embodiments in accompanying with the drawings.

LIST OF REFERENCE NUMERALS

Figure 1:
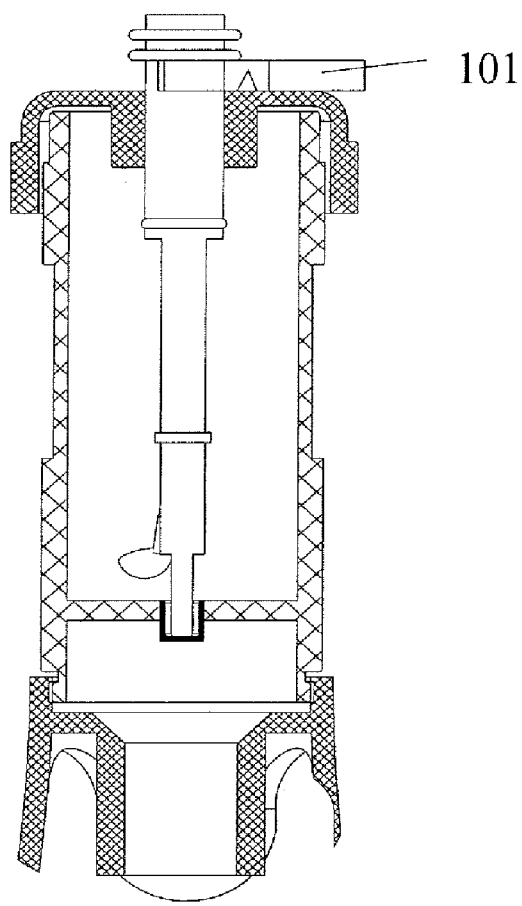
FIG. 1 is a schematic structural view of a disposable feces concentration container in accordance with the prior art.
Figure 2:
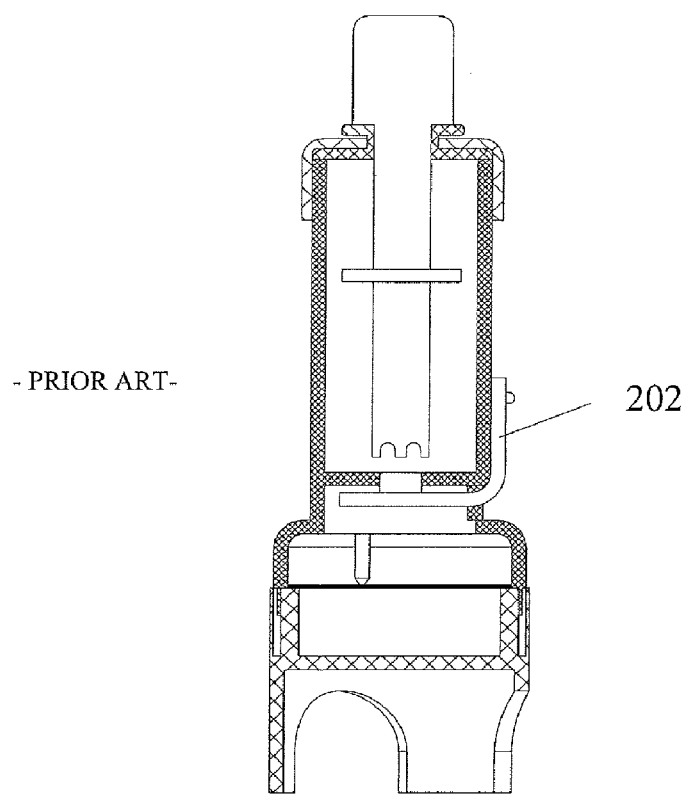
FIG. 2 is a schematic structural view of another disposable feces concentration container in accordance with the prior art.

Seal plug 1
Top cap 2
Cylinder body 3
First layer of filter screen 4
Piston rod 5
Pistons 6
Clutch spring 7
Drainage needle 8
Bottom cap 9
Sampler 10
Second layer of filter screen 11
Middle hole 12
Specimen receiving chamber 13
Receiving container 14

DETAILED DESCRIPTION OF THE INVENTION

Figure 3:
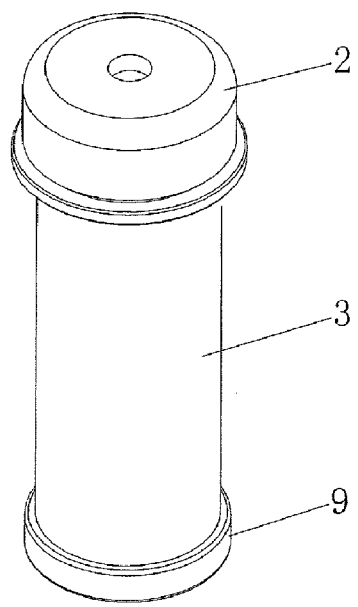
FIG. 3 is a schematic profile view in accordance with the present invention.
Figure 4:
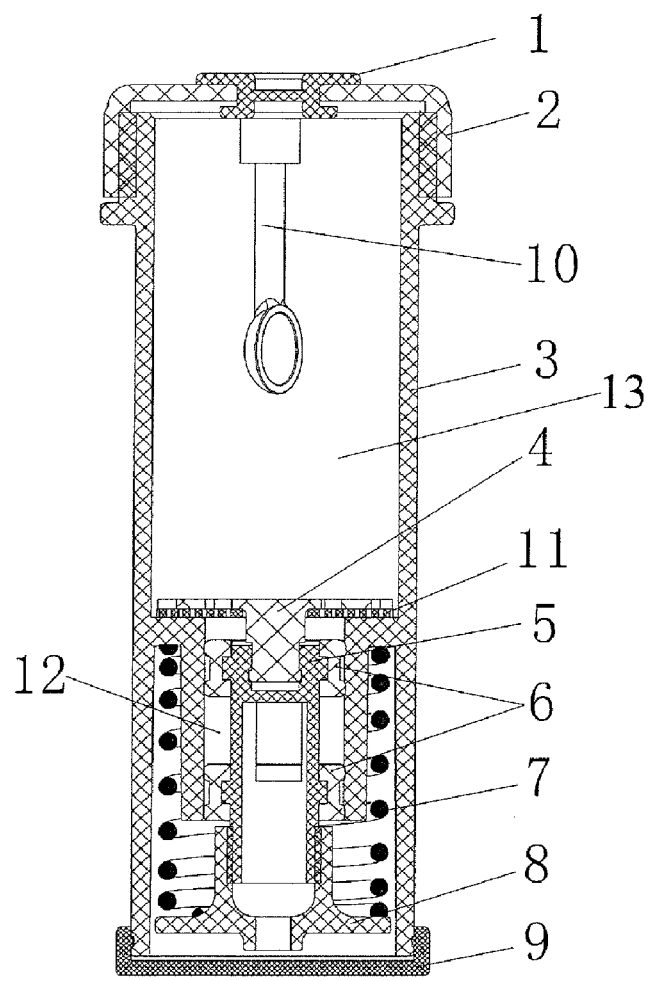
FIG. 4 is a schematic structural view in accordance with the present invention.
Figure 5:
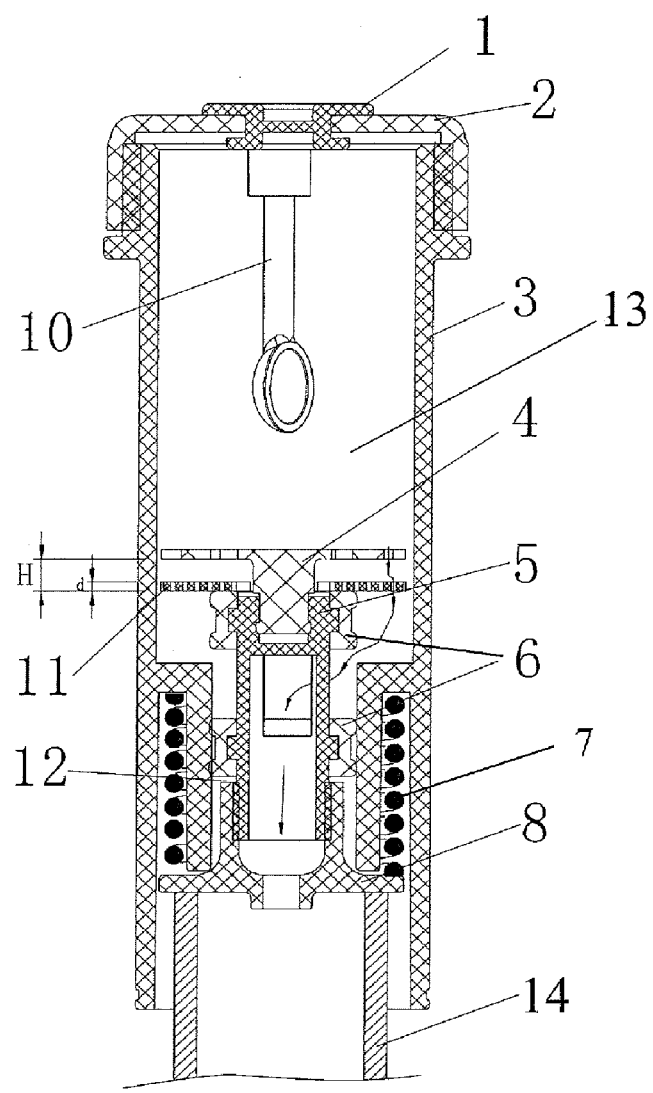
FIG. 5 is a schematic view of a filtering state in accordance with the present invention.
Figure 6:
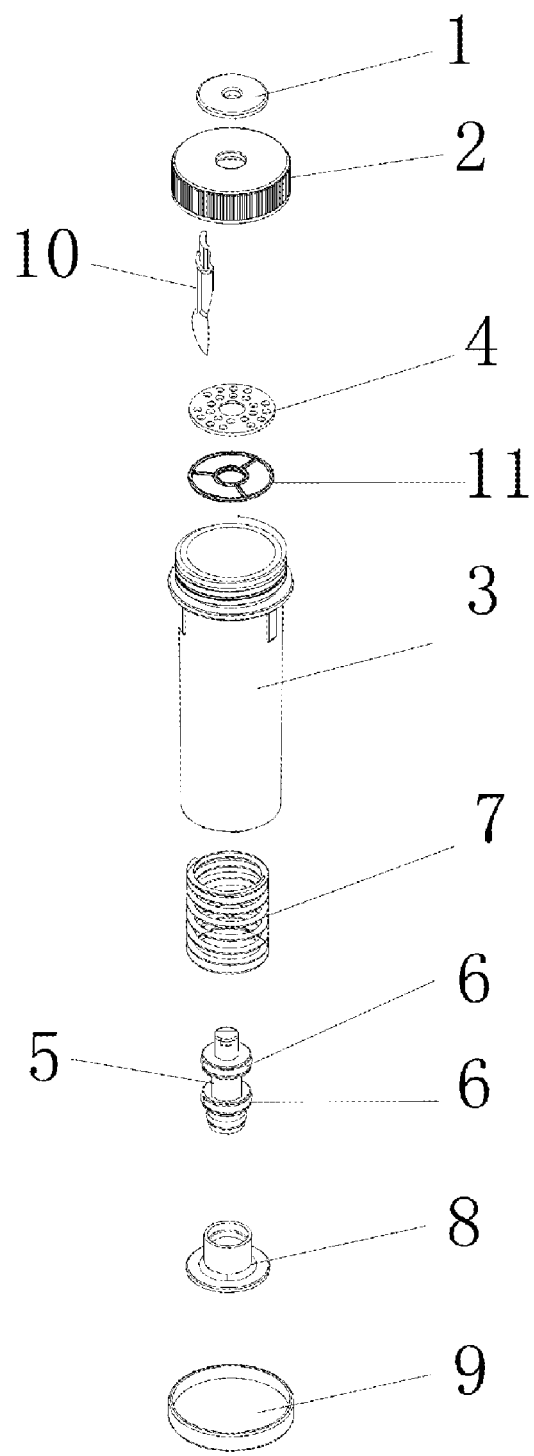
FIG. 6 is an exploded view in accordance with the present invention.

FIGS. 3 to 6 illustrate preferred embodiments of the present invention.

The bottom control type specimen filtering container includes a seal plug 1, a top cap 2, a cylinder body 3, a piston rod 5, pistons 6, a clutch spring 7, a drainage needle 8 and a bottom cap 9. The piston rod 5 is disposed in a middle hole 12 of the bottom of the cylinder body. The pistons 6 are tightly sleeved on the projections of the piston rod 5. The drainage needle 8 is fixedly connected to a lower end of the piston rod 5 through screw thread. One end of the clutch spring 7 is pressed against a bottom of the cylinder body 3 and the other end is pressed against a flange of the drainage needle 8. A double-layer filtering system composed of a first layer of filter screen 4 and a second layer of filter screen 11 is arranged. A shaft of the first layer of filter screen 4 penetrates through a middle hole of the second layer of filter screen 11 and is fixed in a hole defined in a top of the piston rod 5.

The bottom control type specimen filtering container further includes a sampler 10 which is mounted in a designated hole of the top cap 2.

In this embodiment, to maximize the filter result of the double-layer filtering system, a height H of the clearance existing between a lower end surface of the first layer of filter screen 4 and an upper end surface of the pistons 6 is greater than a thickness d of the second layer of filter screen 11.

In use, a solution to be filtered is charged into the filtering container by the sampler 10, and the seal plug 1 may not be used under the condition that a hermetic seal is not required. For a solid specimen (such as feces specimen) that requires the hermetic dissolved filtering, the solid specimen is placed in the container by the sampler 10, and then the seal plug 1 is attached. A soft hole reserved at a center of the seal plug 1 is pierced by a device like a syringe. A liquid for dissolving the solid specimen is charged into the container. Thereafter, the bottom cap 9 is removed and a tube or another receiving container is disposed below the drainage needle 8. The drainage needle 8 is pushed to move upwardly, so as to compress the clutch spring 7 to push the piston rod 5 to thereby drive the pistons 6. The first layer of filter screen 4 moves upwardly, and when moving upwardly for a certain displacement, the second layer of filter screen 11 is pushed by the pistons 6 to move upwardly. Here, a certain room is formed between the first layer of filter screen 4 and the second layer of filter screen 11, thus realizing a double-layer filtering effect. Keep moving the drainage needle 8 upwardly until the specimen in the container drops down through the clearance formed between the upper end surface of the bottom of the cylinder body and the lower end surface of the pistons 6, and then the specimen is drained by the drainage needle 8. When the drainage is stopped, the drainage needle 8 is loosed and returns to the original position by the clutch spring 7. The clearance is stuck by the pistons 6 to prevent the specimen from draining. The present invention has the advantages of sanitation, good sealing property and the capability of the graded filtration of the liquid in the container depending on the requirements.

The above descriptions are merely taken as the preferred embodiment of the present invention, but not intended to restrict the present invention. Any modification, equivalent replacement, and improvement that fall within the spirit and principle of the present invention are included in the protection scope of the claims of the present invention.

What is claimed is:

1. A bottom control specimen filtering apparatus comprising:
   a container comprising:
      a cylinder body having a specimen receiving chamber in an upper portion thereof;
      a top cap having an orifice therein;
      a seal plug received in, and sealing said orifice; and
      a bottom cap;
   a piston rod disposed in a central hole at a lower end of the cylinder body;
   pistons tightly sleeved on projections of the piston rod and engaging the sidewall of said central hole;
   a drainage needle fixedly connected to a lower end of the piston rod by a screw thread;
   a clutch spring, an upper end of which is pressed against a portion of the cylinder body and a lower end of which is pressed against a flange of the drainage needle; and
   a double-layer filtering system composed of a first layer of filter screen and a second layer of filter screen, wherein a shaft of the first layer of filter screen penetrates through a middle hole of the second layer of filter screen and is fixed in a hole at the top of the piston rod, an upper surface of said first layer defining a lower end of said specimen receiving chamber.

2. The bottom control specimen filtering apparatus of claim 1, further comprising a sampler mounted within said cylinder body and in fluid communication with said orifice in said top cap.

3. The bottom control specimen filtering apparatus of claim 1, wherein a clearance exists between a lower end surface of the first layer of filter screen and an upper end surface of the pistons, and a height of the clearance is greater than a thickness of the second layer of filter screen.

4. The bottom control specimen filtering apparatus of claim 1, wherein said central hole is defined by an integral projection of said cylinder body.

5. The bottom control specimen filtering apparatus of claim 4, wherein said clutch spring is located in an annular region between a wall of said cylindrical body and said integral projection.

* * * * *